United States Patent
Ortiz

(10) Patent No.: US 7,452,363 B2
(45) Date of Patent: Nov. 18, 2008

(54) APPLIER FOR FASTENER FOR SINGLE LUMEN ACCESS ANASTOMOSIS

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 681 days.

(21) Appl. No.: 10/675,077

(22) Filed: Sep. 30, 2003

(65) Prior Publication Data

US 2005/0070926 A1    Mar. 31, 2005

(51) Int. Cl.
*A61B 17/10* (2006.01)
(52) U.S. Cl. .................. 606/139; 606/153
(58) Field of Classification Search .............. 606/153, 606/139, 151, 157, 198; 600/201, 207; 604/109–113
See application file for complete search history.

(56) References Cited

U.S. PATENT DOCUMENTS

| | | |
|---|---|---|
| 2,004,013 A | 6/1935 | Reed |
| 2,004,014 A | 6/1935 | Sanford |
| 2,004,172 A | 6/1935 | Niday |
| 4,841,888 A | 6/1989 | Mills et al. |
| 5,041,129 A | 8/1991 | Hayhurst et al. |
| 5,080,663 A | 1/1992 | Mills et al. |
| 5,217,486 A | 6/1993 | Rice et al. |
| 5,269,809 A | 12/1993 | Hayhurst et al. |
| 5,376,101 A | 12/1994 | Green et al. |
| 5,398,670 A | 3/1995 | Ortiz et al. |
| 5,437,681 A | 8/1995 | Meade et al. |
| 5,462,558 A | 10/1995 | Kolesa et al. |
| 5,464,415 A | 11/1995 | Chen |
| 5,503,635 A | 4/1996 | Sauer et al. |
| 5,514,159 A | 5/1996 | Matula et al. |
| 5,540,705 A | 7/1996 | Meade et al. |
| 5,571,119 A | 11/1996 | Atala |
| 5,584,861 A | 12/1996 | Swain et al. |
| 5,649,938 A | 7/1997 | Allen et al. |
| 5,676,670 A | 10/1997 | Kim |

(Continued)

FOREIGN PATENT DOCUMENTS

RU    2208400    7/2003

(Continued)

OTHER PUBLICATIONS

USPTO Non-Final Rejection for U.S. Appl. No. 10/675,705, dated May 4, 2007.

(Continued)

*Primary Examiner*—Melissa Ryckman
(74) *Attorney, Agent, or Firm*—Frost Brown Todd LLC

(57) ABSTRACT

Creating an anastomosis, or the surgical formation of a passage between two normally distinct vessels or lumens, is enhanced by an applier that introduces a ring device without the need for a separate anvil to form a hollow rivet shaped attachment. Moreover, the ring device may be advantageously formed in a cylindrical shape from molded polymer material or stamped from sheet metal with proximal and distal rings connected by proximal and distal arms that respectively form hinged, ring shaped so appose tissue walls. A center ring or portion sits in the attachment site. The applier causes actuating by moving the rings relative to one another. A latching mechanism locks the rings in the actuating state.

11 Claims, 7 Drawing Sheets

U.S. PATENT DOCUMENTS

| | | | |
|---|---|---|---|
| 5,709,693 A | 1/1998 | Taylor | |
| 5,713,910 A | 2/1998 | Gordon et al. | |
| 5,755,730 A | 5/1998 | Swain et al. | |
| 5,797,920 A | 8/1998 | Kim | |
| 5,814,071 A | 9/1998 | McDevitt et al. | |
| 5,843,088 A | 12/1998 | Barra et al. | |
| 5,853,422 A * | 12/1998 | Huebsch et al. | 606/213 |
| 5,860,992 A | 1/1999 | Daniel et al. | |
| 5,868,760 A | 2/1999 | McGuckin | |
| 5,887,594 A | 3/1999 | LoCicero, III | |
| 5,899,921 A | 5/1999 | Caspari et al. | |
| 5,902,321 A | 5/1999 | Caspari et al. | |
| 5,954,731 A | 9/1999 | Yoon | |
| 6,007,544 A | 12/1999 | Kim | |
| 6,010,515 A | 1/2000 | Swain et al. | |
| 6,036,694 A | 3/2000 | Goble et al. | |
| 6,200,329 B1 | 3/2001 | Fung et al. | |
| 6,312,446 B1 | 11/2001 | Huebsch et al. | |
| 6,346,111 B1 | 2/2002 | Gordon et al. | |
| 6,358,259 B1 | 3/2002 | Swain et al. | |
| 6,379,368 B1 | 4/2002 | Corcoran et al. | |
| 6,443,962 B1 | 9/2002 | Gaber | |
| 6,454,778 B2 | 9/2002 | Kortenbach | |
| 6,461,320 B1 | 10/2002 | Yencho et al. | |
| 6,494,888 B1 | 12/2002 | Laufer et al. | |
| 6,500,195 B2 | 12/2002 | Bonutti | |
| 6,506,196 B1 | 1/2003 | Laufer | |
| 6,524,328 B2 | 2/2003 | Levinson | |
| 6,540,789 B1 | 4/2003 | Silverman et al. | |
| 6,543,456 B1 | 4/2003 | Freeman | |
| 6,558,400 B2 | 5/2003 | Deem et al. | |
| 6,572,629 B2 | 6/2003 | Kalloo et al. | |
| 6,632,227 B2 * | 10/2003 | Adams | 606/110 |
| 6,663,639 B1 | 12/2003 | Laufer et al. | |
| 6,709,441 B2 | 3/2004 | Bolduc et al. | |
| 6,712,836 B1 | 3/2004 | Berg et al. | |
| 6,719,763 B2 | 4/2004 | Chung et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,858 B2 | 11/2004 | Namatame et al. | |
| 6,835,200 B2 | 12/2004 | Laufer et al. | |
| 6,869,395 B2 | 3/2005 | Page et al. | |
| 6,908,427 B2 | 6/2005 | Fleener et al. | |
| 6,949,116 B2 | 9/2005 | Solymar et al. | |
| 6,955,643 B2 | 10/2005 | Gellman et al. | |
| 7,004,949 B2 | 2/2006 | Yencho et al. | |
| 2001/0023352 A1 | 9/2001 | Gordon et al. | |
| 2002/0107530 A1 | 8/2002 | Sauer et al. | |
| 2002/0193809 A1 | 12/2002 | Meade et al. | |
| 2003/0032967 A1 | 2/2003 | Park et al. | |
| 2003/0083674 A1 | 5/2003 | Gibbens | |
| 2003/0109900 A1 | 6/2003 | Martinek | |
| 2003/0120265 A1 | 6/2003 | Deem et al. | |
| 2003/0120292 A1 | 6/2003 | Park et al. | |
| 2003/0171760 A1 | 9/2003 | Gambale | |
| 2003/0181924 A1 | 9/2003 | Yamamoto et al. | |
| 2003/0191481 A1 | 10/2003 | Nguyen et al. | |
| 2003/0225312 A1 | 12/2003 | Suzuki et al. | |
| 2003/0229296 A1 | 12/2003 | Ishikawa et al. | |
| 2003/0233104 A1 | 12/2003 | Gellman et al. | |
| 2003/0233108 A1 | 12/2003 | Gellman et al. | |
| 2004/0002720 A1 | 1/2004 | Kortenbach et al. | |
| 2004/0006351 A1 | 1/2004 | Gannoe et al. | |
| 2004/0024386 A1 | 2/2004 | Deem et al. | |
| 2004/0034369 A1 | 2/2004 | Sauer et al. | |
| 2004/0059350 A1 | 3/2004 | Gordon et al. | |
| 2004/0082963 A1 | 4/2004 | Gannoe et al. | |
| 2004/0098050 A1 | 5/2004 | Foerster et al. | |
| 2004/0122452 A1 | 6/2004 | Deem et al. | |
| 2004/0122453 A1 | 6/2004 | Deem et al. | |
| 2004/0122473 A1 | 6/2004 | Ewers et al. | |
| 2004/0147958 A1 | 7/2004 | Lam et al. | |
| 2004/0162568 A1 | 8/2004 | Saadat et al. | |
| 2004/0193184 A1 | 9/2004 | Laufer et al. | |
| 2004/0194790 A1 | 10/2004 | Laufer et al. | |
| 2004/0210243 A1 | 10/2004 | Gannone et al. | |
| 2004/0215058 A1 | 10/2004 | Zirps et al. | |
| 2005/0015101 A1 | 1/2005 | Gibbens et al. | |
| 2005/0033319 A1 | 2/2005 | Gambale et al. | |
| 2005/0055038 A1 | 3/2005 | Kelleher et al. | |
| 2005/0070921 A1 | 3/2005 | Ortiz et al. | |
| 2005/0070926 A1 | 3/2005 | Ortiz | |
| 2005/0070931 A1 | 3/2005 | Li et al. | |
| 2005/0070934 A1 | 3/2005 | Tanaka et al. | |
| 2005/0070935 A1 | 3/2005 | Ortiz | |
| 2005/0070939 A1 | 3/2005 | Beaupre | |
| 2005/0075653 A1 | 4/2005 | Saadat et al. | |
| 2005/0075654 A1 | 4/2005 | Kelleher | |
| 2005/0143760 A1 | 6/2005 | Imran | |
| 2005/0143762 A1 | 6/2005 | Paraschac et al. | |
| 2005/0149067 A1 | 7/2005 | Takemoto et al. | |
| 2005/0165419 A1 | 7/2005 | Sauer et al. | |
| 2005/0192599 A1 | 9/2005 | Demaris | |
| 2005/0192601 A1 | 9/2005 | Demaris | |
| 2005/0203488 A1 | 9/2005 | Michlitsch et al. | |
| 2006/0217748 A1 | 9/2006 | Ortiz | |

FOREIGN PATENT DOCUMENTS

| | | |
|---|---|---|
| WO | WO-95/19140 | 7/1995 |
| WO | WO 99/17662 | 4/1999 |
| WO | WO-00/61013 | 10/2000 |
| WO | WO-01/10312 | 2/2001 |
| WO | WO-01/66001 | 9/2001 |
| WO | WO-01/89393 | 11/2001 |
| WO | WO-02/096327 | 12/2002 |
| WO | WO 03/000142 | 1/2003 |
| WO | WO-2004/021894 | 3/2004 |
| WO | WO-2005/034729 | 4/2005 |

OTHER PUBLICATIONS

USPTO Final Rejection for U.S. Appl. No. 10/675,705, dated Jan. 24, 2007.
USPTO Non-Final Rejection for U.S. Appl. No. 10/675,705, dated Aug. 7, 2006.
USPTO Non-Final Rejection for U.S. Appl. No. 10/675,705, dated Feb. 27, 2006.
USPTO Office Action for U.S. Appl. No. 10/675,705, dated Jan. 10, 2006.
EPO Search Report for Application No.: 04256046.6, dated Feb. 9, 2005.
EPO Communication for Application No.: 04256046.6, dated Dec. 27, 2005.
EPO Communication dor Application No.: 04256046.6, dated Oct. 17, 2006.
EPO Search Report for Application No.: 04256018.5, dated Dec. 22, 2004.

* cited by examiner

APPLIER FOR FASTENER FOR SINGLE LUMEN ACCESS ANASTOMOSIS

CROSS REFERENCE TO RELATED APPLICATIONS

The present application is related to four co-pending and commonly-owned applications filed on even date herewith, the disclosure of each is hereby incorporated by reference in its entirety:

"Anastomosis Wire Ring Device", Ser. No. 10/674,371 to Don Tanaka, Mark Ortiz and Darrel Powell;

"Unfolding Anastomosis Ring Device", Ser. No. 10/675,091 to Jean Beaupre;

"Single Lumen Access Deployable Ring for Intralumenal Anastomosis", Ser. No. 10/675,075 to Mark Ortiz; and "Single Lumen Anastomosis Applier for Fastener", Ser. No. 10/675,497 to Mark Ortiz, Robert MeKenna, Bill Kramer, Mike Stokes, and Foster Stulen.

FIELD OF THE INVENTION

The present invention relates, in general, to devices and methods for surgically modifying organs and vessels. More particularly, it relates to anastomosis devices for joining two organs such as, for example, two separate lengths of small bowel to each other, a section of small bowel to the stomach, or the common bile duct to the duodenum in a procedure called a choledochoduodenostomy. Vascular anastomosis may be performed as well.

BACKGROUND OF THE INVENTION

The percentage of the world population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacological methods have all been tried, and though temporarily effective, failed to correct the condition. Further, introducing an object in the stomach, such as an esophago-gastric balloon, to fill the stomach have also been used to treat the condition; however, such approaches tend to cause irritation to the stomach and are not effective long-term.

Surgical treatments of morbid obesity have been increasingly used with greater success. These approaches may be generalized as those that reduce the effective size of the stomach, limiting the amount of food intake, and those that create malabsorption of the food that it is eaten. For instance, some patients benefit from adjustable gastric bands (AGB) that are advantageously laparoscopically placed about the stomach to form a stoma of a desired size that allows food to fill an upper portion of the stomach, causing a feeling of satiety. To allow adjustment of the size of the stoma after implantation, a fluid conduit communicates between an inwardly presented fluid bladder of the AGB to a fluid injection port subcutaneously placed in front of the patient's sternum. A syringe needle may then inject or withdraw fluid as desired to adjust the AGB.

Although an effective approach to obesity for some, other patients may find the lifestyle changes undesirable, necessitated by the restricted amount of food intake. In addition, the medical condition of the patient may suggest the need for a more permanent solution. To that end, surgical approaches have been used to alter the portions of the stomach and/or small intestine available for digesting food. Creating an anastomosis, or the surgical formation of a passage between two normally distinct vessels, is a critical step of many surgical procedures. This is particularly true of gastric bypass procedures in which two portions of small intestine are joined together and another portion of small intestine is joined to the stomach of the patient. This is also true of surgery to alleviate blockage in the common bile duct by draining bile from the duct to the small intestine during surgery for pancreatic cancer.

With particular reference to gastric bypass procedures, current methods of performing a laparoscopic anastomoses for a gastric bypass include stapling, suturing, and placing biofragmentable rings, each having significant challenges. For instance, suturing is time consuming, as well as being technique and dexterity dependent. Stapling requires placement of an anvil, which is a large device that cannot be introduced through a trocar port. Having to introduce the port through a laparotomy presents an increased incidence of wound site infection associated with Intralumenal content being dragged to the laparotomy entry site.

As an example of the latter approach, in U.S. Pat. No. 6,543,456 a method for gastric bypass surgery includes the insertion of proximal and distal anastomosis members (e.g., anvils) transorally with grasping forceps. The stomach and the small intestine are transected endoscopically by a surgical severing and stapling instrument to create a gastric pouch, a drainage loop, and a Roux limb. An endoscopically inserted circular stapler attaches to the distal anastomosis member to join the drainage loop to a distal portion of the intestine, and the circular stapler attaches to the proximal anastomosis member to join the Roux limb to the gastric pouch. Thereafter, the anastomosis members are removed to create an orifice between joined portions of the stomach and intestine. This method reduces the number of laparoscopic ports, avoids a laparoscopic insertion of an anastomosis instrument (e.g., circular stapler) into an enlarged surgical port, and eliminates the need for an enterotomy and an enterotomy closure.

For many anastomoses, surgeons use circular staplers, linear staplers, or manual sutures. However, to reduce incision size and to make the surgical process less technically demanding and time consuming, an anastomotic device that deforms to hold tissue portions together when the device is ejected from a constraining enclosure has been described. Such an approach is described in U.S. patent application Publ. No. US 2003/0032967 and PCT application WO 03/000142 both to Adrian Park et al, which is hereby incorporated herein by reference, describes such a device. Therein, gastrointestinal or enteric (including biliary) anastomosis is achieved by insertion of a sheath that perforates the walls of two tissue passages, such as the stomach and small intestine. A three-dimensional woven tube of wire of having a thermal shape memory effect (SME) ("generally-known nitinol ring device") is presented by a cannula of the sheath on both sides of the openings. Deployment of the woven tube causes the outer loops or ends of the tube to fold or loop back to hold the luminal interface of the anastomosis site in apposition. Thereby, the need for a mechanical compression component in a delivery system is reduced or avoided, reducing the size and complexity of the delivery device.

The anastomotic device disclosed in WO 03/000142 is constrained by a retractable sheath to an advantageous small-diameter tubular shape. A surgeon applies the anastomotic device by maneuvering the sheath through the tissue portions requiring anastomosis and retracting the sheath. Retracting the sheath removes the constraint on the device, allowing the device to assume a roughly hourglass shape. The larger ends of the hourglass shape hold the two tissue portions together in an effective anastomosis.

The constrained anastomotic device, which may be made of a shape memory material such as nitinol, exerts a force against the inner diameter of the sheath and tends to warp towards its roughly hourglass-shaped deployed position. When the sheath is retracted proximally, the forces generated by the device in transition from a tubular shape to an hourglass shape urge the anastomotic device distally. This device movement makes surgical control harder to achieve when placing the device through the otomies of two tissue portions requiring anastomosis.

While the generally-known nitinol ring device is a significant advancement in the treatment of morbid obesity, it is believed that further improvements would be desirable. For instance, weaving the wire strands and fastening together the ends and heat treating the woven tubes into an SME device is expensive. In addition, it may tend to be difficult to maintain two lumens that are to be anastomotized in extremely close contact in order for the generally-known nitinol ring device to successfully attach to both sides. Having to insert one or more grasping tools along with the anastomosis ring applier tends to mitigate the advantages of a single lumen anastomosis by requiring multiple access ports. Moreover, even if the lumens are proximately position, the generally-known nitinol ring device tends to actuate slowly, if at all, by being limited to SME actuation.

Consequently, there is a general need for an device for single lumen access anastomosis that can be used in existing trocar ports (e.g., 12 mm size) and that reliably and effectively creates an anastomotic attachment between lumens, eliminating the need for surgical stapling and suturing to form an anastomosis.

BRIEF SUMMARY OF THE INVENTION

The invention overcomes the above-noted and other deficiencies of the prior art by providing an applier for an absorbable ring for a single lumen access anastomosis, the combination being suitable and sufficient to perform lumen control and apposition as well as enterotomy control. The applier then may be inserted through a trocar and applied without any additional parts such as an anvil. The applier holds the absorbable ring that has distal and proximal arm segments that the applier individually actuates to enhance control. For instance, the distal arm segments may be expanded in a distal lumen, which is then drawn back into closer contact with the proximal lumen before actuating the proximal arm segment. Alternatively, the proximal arm segments may be expanded first and the first lumen positioned relative to the second lumen. Thereby, positioning the two lumens to be anastomotized is simplified.

In one aspect of the invention, an applier has an implement portion that receives an anastomosis ring device with an unactuated shape of a cylinder with a proximal ring at one end and a distal ring at the other. The ring device further has proximal arms that are attached to the proximal ring and has distal arms are attached to the distal ring. Inwardly directed ends of the distal arms are coupled to inwardly directed ends of the proximal arms at a center ring such that the arms will outwardly actuate when the rings are drawn closer together during actuation. The ring device has a latching mechanism that locks the rings in this actuated shape of a rivet. The applier engages the ring such that the spacing of the distal ring to the center ring and the spacing of the proximal ring to the center ring may be reduced, causing actuation and latching. Then, the implement portion is removed from the ring device. Thus, a single lumen procedure is achieved without the need for a separate anvil device to actuate the device. Moreover, since the applier affirmatively actuates the ring device, limitations of generally-known shape memory effect (SME) actuation of a wire stent-like ring device are avoided.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
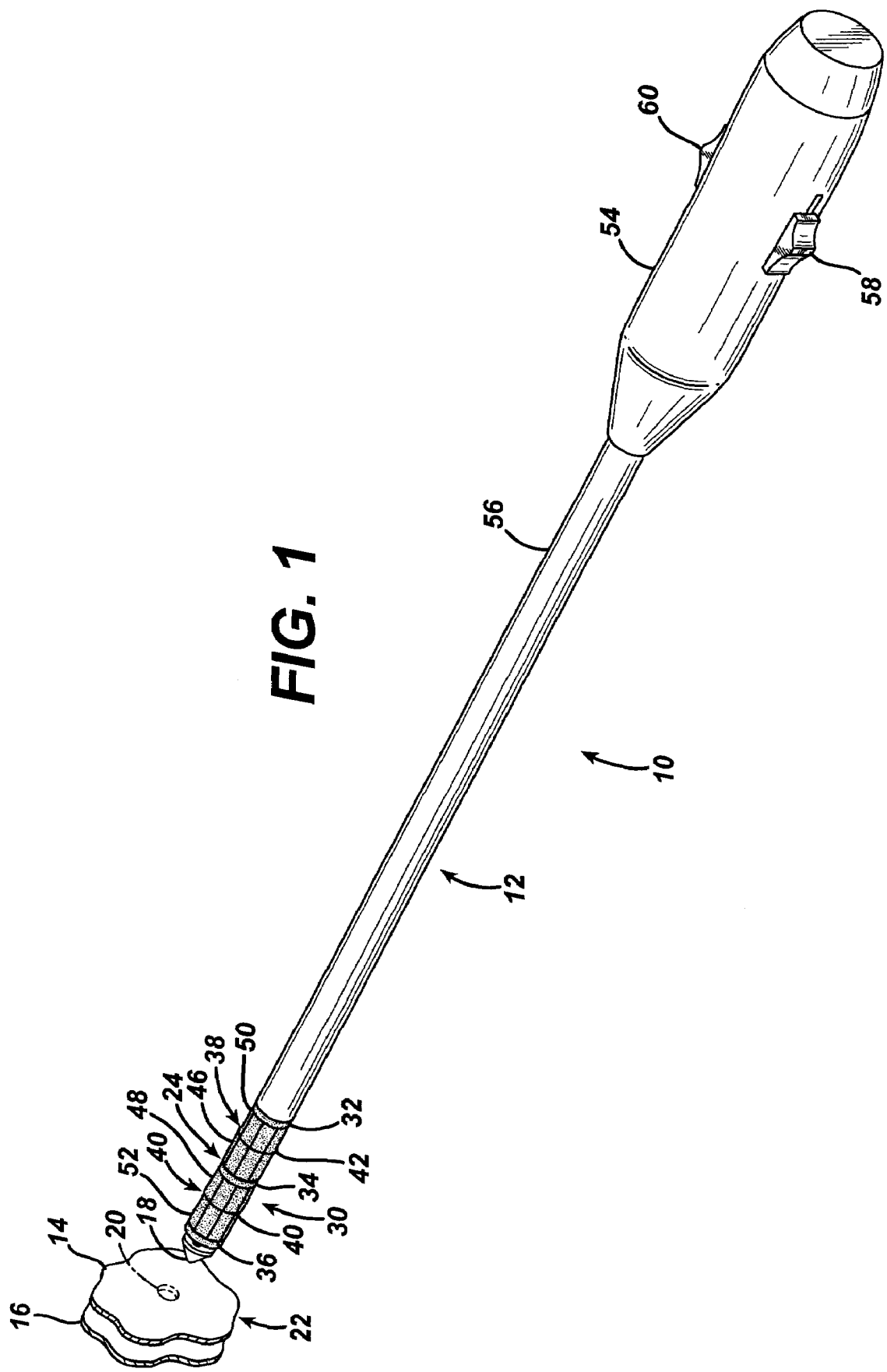
FIG. 1 is perspective view of an single lumen access deployable ring for Intralumenal anastomosis installed upon an applier being inserted laparoscopically to an anastomosis target site on each of two portions of a patient's small intestine.

Turning to the Drawings, wherein like numerals denote like components throughout the several views, FIG. 1 depicts an applier 10 having an elongate implement portion 12 dimensionally sized for insertion through a cannula of a trocar or laparoscopic port to tissues walls 14, 16 to anastomose two lumens. A distal introducer tip 18 of the applier 10 pierces through an opening 20 at an anastomosis site 22 to position an actuating portion 24 that holds a ring device 30 for single lumen anastomosis.

The ring device 30 has three primary rings, depicted as a proximal ring 32, a center ring 34, and a distal ring 36, that are cylindrically aligned with one another. The proximal ring 32 is longitudinally attached to the center ring 34 by proximal arms 38, which in turn is longitudinally attached to the distal ring 36 by distal arms 40. Each proximal and distal arm 38, 40 is bisected respectively by a hinged joint 42, 44 defining an inner arm segment 46, 48 also hingedly attaching to the center ring 34 and an outer arm segment 50, 52 also hingedly attached to the respective proximal or distal ring 32, 36. In its unactuated state as depicted in FIG. 1, the device 30 is cylindrical. The relative lengths of the inner arm segments 46, 48 to outer arm segments 50, 52 may be selected to provide a desired angular contact to tissue walls 14, 16. In the illustrative version, the relationship resembles a cantilevered contact with the inner arm segments 46, 48 actuating to an approximately parallel relationship to the tissue walls 14, 16.

A handle portion 54 is proximally connected to a shaft 56 of the implement portion 12. The shaft 56 may be rigid or flexible, with the latter being desirable for Intralumenal insertion, such as through the esophagus. The handle includes controls for longitudinally positioning the rings 32-36 of the ring device 30. In the illustrative version, this includes a center ring slide control 58 and a distal ring slide control 60. Although a manually positioned and actuated applier 10 is depicted for clarity, it should be appreciated that a remotely positioned and actuated applier may be used consistent with aspects of the invention, for instance to allow placement in a more controlled manner, to avoid disturbing an imaging modality, or for other reasons. The handle 54 may further include controls for a distal tip illumination capability so that actuation of the distal arms 40 in the distal lumen may be proximally viewed from an endoscope. It will be appreciated that the terms "proximal" and "distal" are used herein with reference to a clinician gripping the handle portion 54 of the applier 10.

Figure 2:
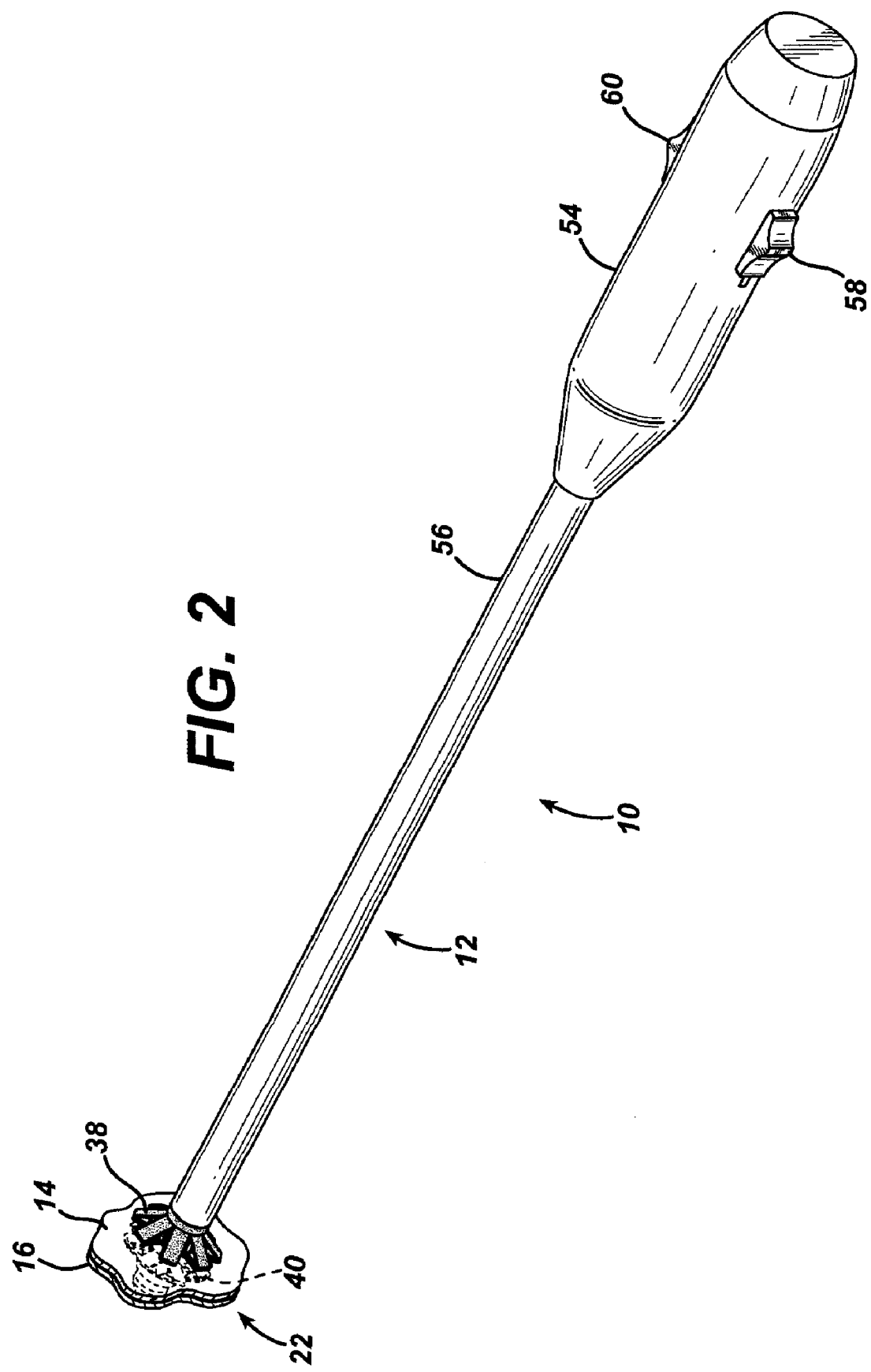
FIG. 2 is the applier of FIG. 1 after actuation of the single lumen access deployable ring to appose the two portions of small intestine.

In FIG. 2, two slide controls 58, 62 have been withdrawn proximally, bringing both the center and distal rings 34, 36 into locking proximity of the proximal ring 32, which is held in place by resting against the shaft 56. In response thereto, the proximal and distal arms 38, 40 hinge outwardly from the longitudinal axis of the device 30, creating a hollow rivet or hourglass shape for apposing tissue walls 14, 16. The center ring 34 sits at a tissue junction between lumens and the distal and proximal rings 32, 36 come to rest in respective lumens. By latching rings 32-38 one to another when actuated, the device 30 is held in the actuated position with bent arms 38, 40 apposing tissue. The proximal arms 38 may be staggered, as depicted, from distal arms 40 to create a tortuous path for the compressed tissue. Alternatively, the arms 38, 40 may be aligned to directly mate to each other.

It should be appreciated that in the illustrative version, the proximal ring 36 is stationary with respect to the applier 10. In some applications, a third control may be incorporated so that each of the three rings may be positioned independently from the rest, further enhancing the ability to actuate either the distal or the proximal arms 40, 38. As another alternative, the center ring 34 may be stationary with respect to the applier 10, with controls effective to move the proximal and distal rings 32, 36 inwardly to the center ring 34.

Figure 3:
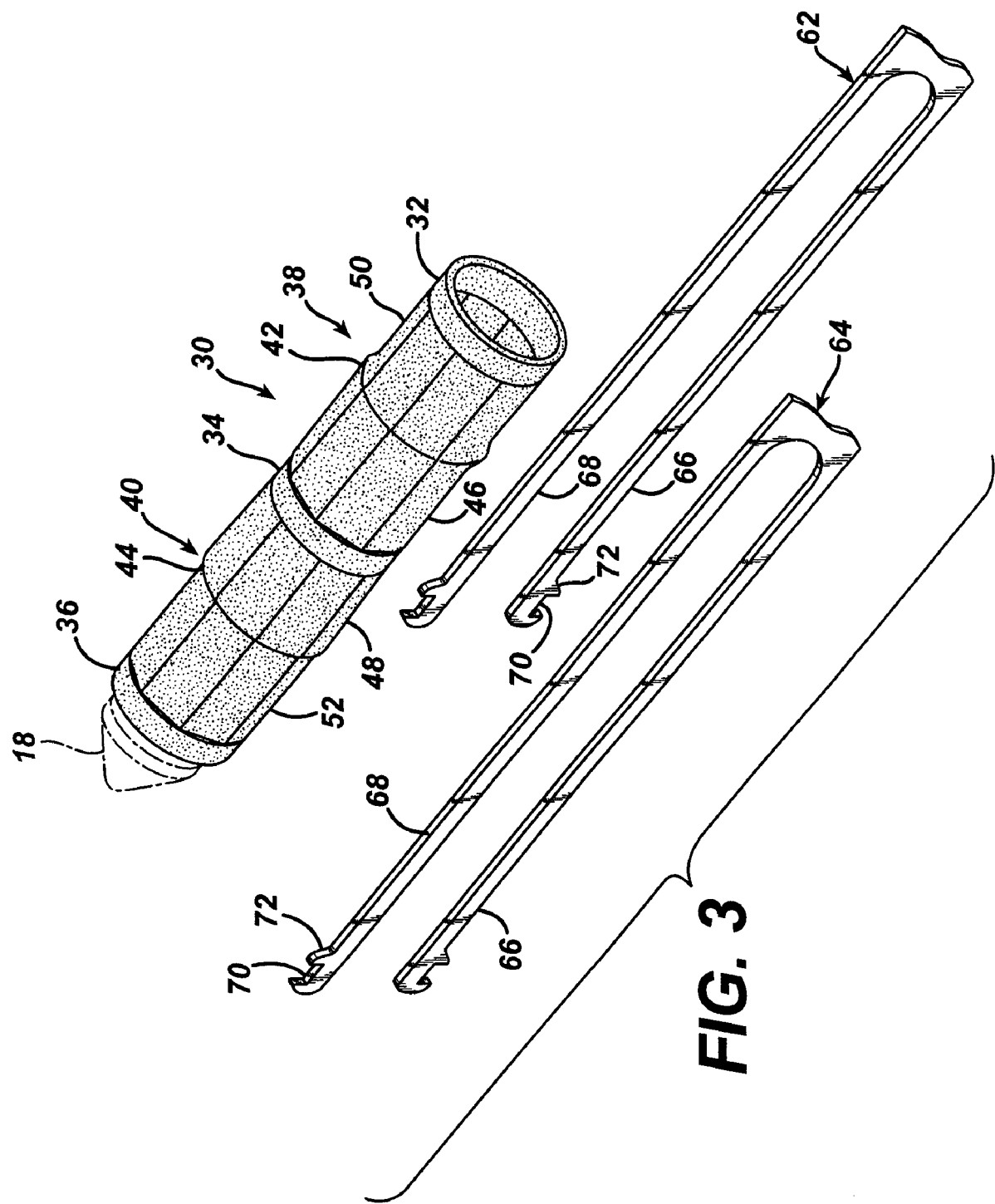
FIG. 3 is a detail view of the unactuated single lumen access deployable ring and distal tip and catches of the applier.

In FIG. 3, the unactuated ring device 30 is shown with the distal introducer tip 18 of the applier 10. The ring device 10 may be comprised of a single piece of molded or stamped material. For instance, the ring device 10 may be advantageously formed from a stamped piece of sheet metal that is wound around a mandrel and tack welded into a cylindrical shape. Cuts define the arms 38, 40 and creases define the hinged portions. Similar manufacturing economies may be achieved by molding the ring device 30 from a polymeric material. Furthermore, the device 10 may be formed entirely or partially of a biofragmentable or absorbable material to assist in the eventual passing of the device 10, leaving a patent anastomosis. The ring device 10 may advantageously include radiopaque markers in the arms to allow diagnostic imaging to confirm placement of the device 10 and/or to confirm passing. It should be appreciated that the afore-described methods of manufacture are believed to yield economical and therapeutic advantages; however, other techniques for fabrication and assembly may be employed.

Also depicted in FIG. 3, a center ring actuating member 62 and a distal ring actuating member 64 are shown that move within the shaft 56 in response to the center and distal ring slide controls 58, 60. In the illustrative version, each actuating member 62, 64 is formed from a rigid polymer or sheet metal to have two parallel elongate prongs 66, 68 springedly outwardly biased or urged outwardly by other portions of the applier 10 to present distally and laterally presented catches 70 to the inner surface of their respective rings for engagement. Proximal to each catch 70 is a releasing ramp 72 that causes the catch 70 to move inwardly as the releasing ramp 72 contacts the next more proximal ring at or near full actuation. Thus, the ring device 30 is disengaged from the actuating portion 24 of the applier 10 and may be deployed.

Figure 4:
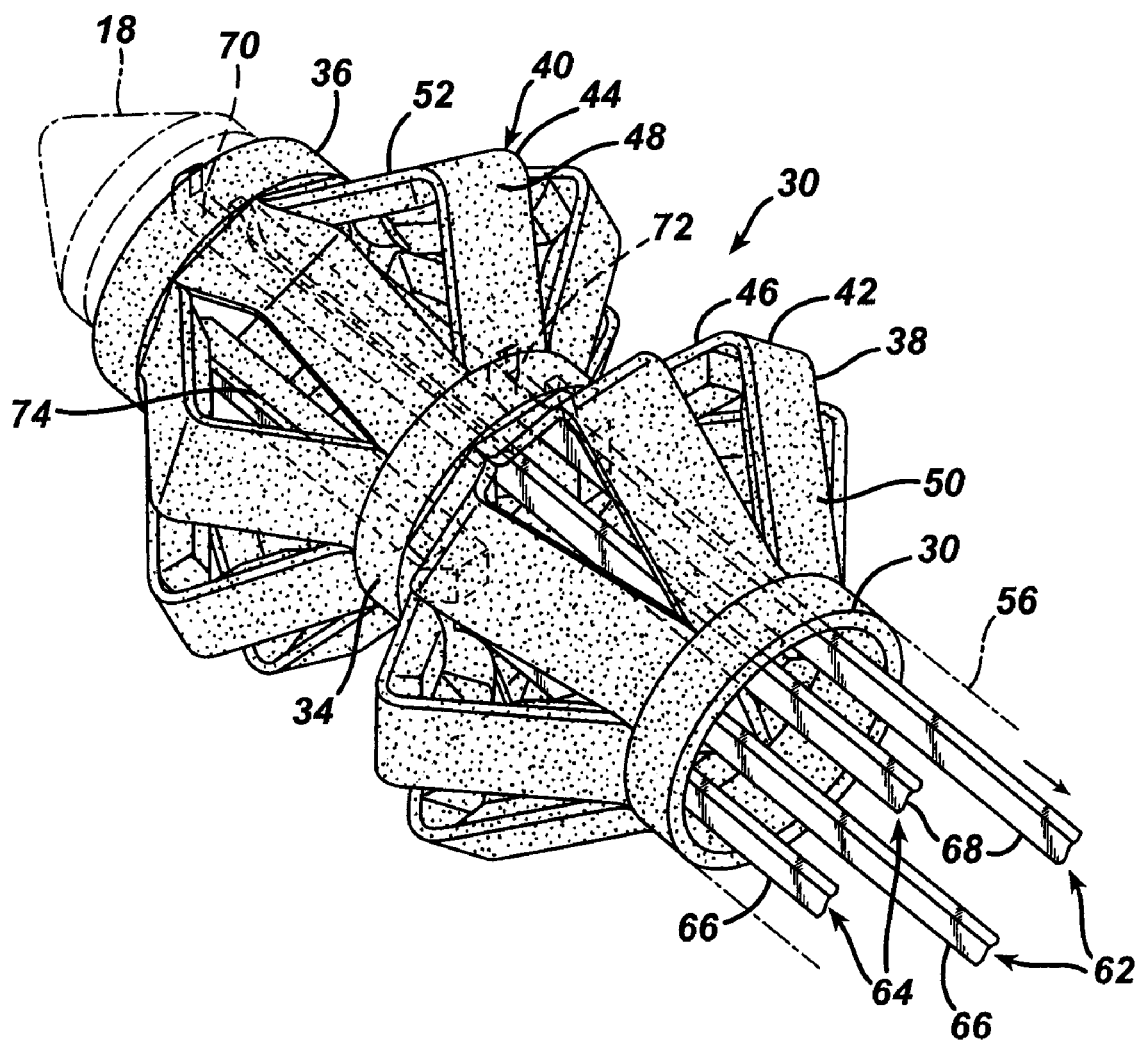
FIG. 4 is a perspective detail view of a partially-actuated ring device and the catches and distal tip of the applier of FIG. 2.
Figure 5:
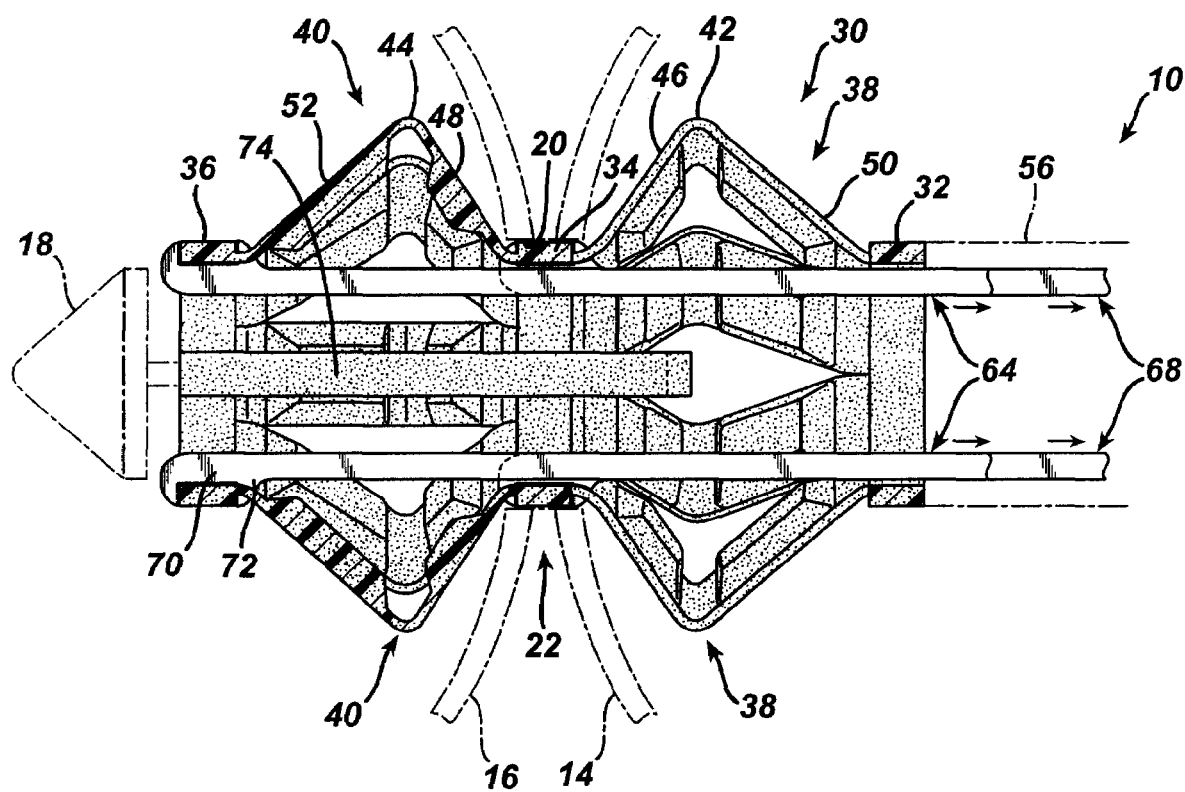
FIG. 5 is a side elevation detail view of the partially-actuated ring device and distal portion of the applier of FIG. 2 cutaway along the longitudinal axis.

In FIGS. 4-5, the actuating members 62, 64 are depicted as having moved proximally to an intermediate locking position. The shaft 56 (shown in phantom) has restrained the proximal ring 32 while center ring actuating member 62 has drawn back the center ring 34 such that the proximal arms 38 have partially actuated. Similarly, the distal ring actuating member 64 has drawn back the distal ring 36 such that the relative distance between the distal and center 36, 34 is sufficient to also partially actuate the distal arms 40. A locking mechanism, depicted as proximally directed locking hook 74, is connected to the distal ring 36 and is depicted as transitioning past the center ring 34 at this intermediate actuating position. It may be desired in some applications for there to be sufficient interference or latching at intermediate points during actuation for the ring device 30 to remain in a partially actuated position.

Figure 6:
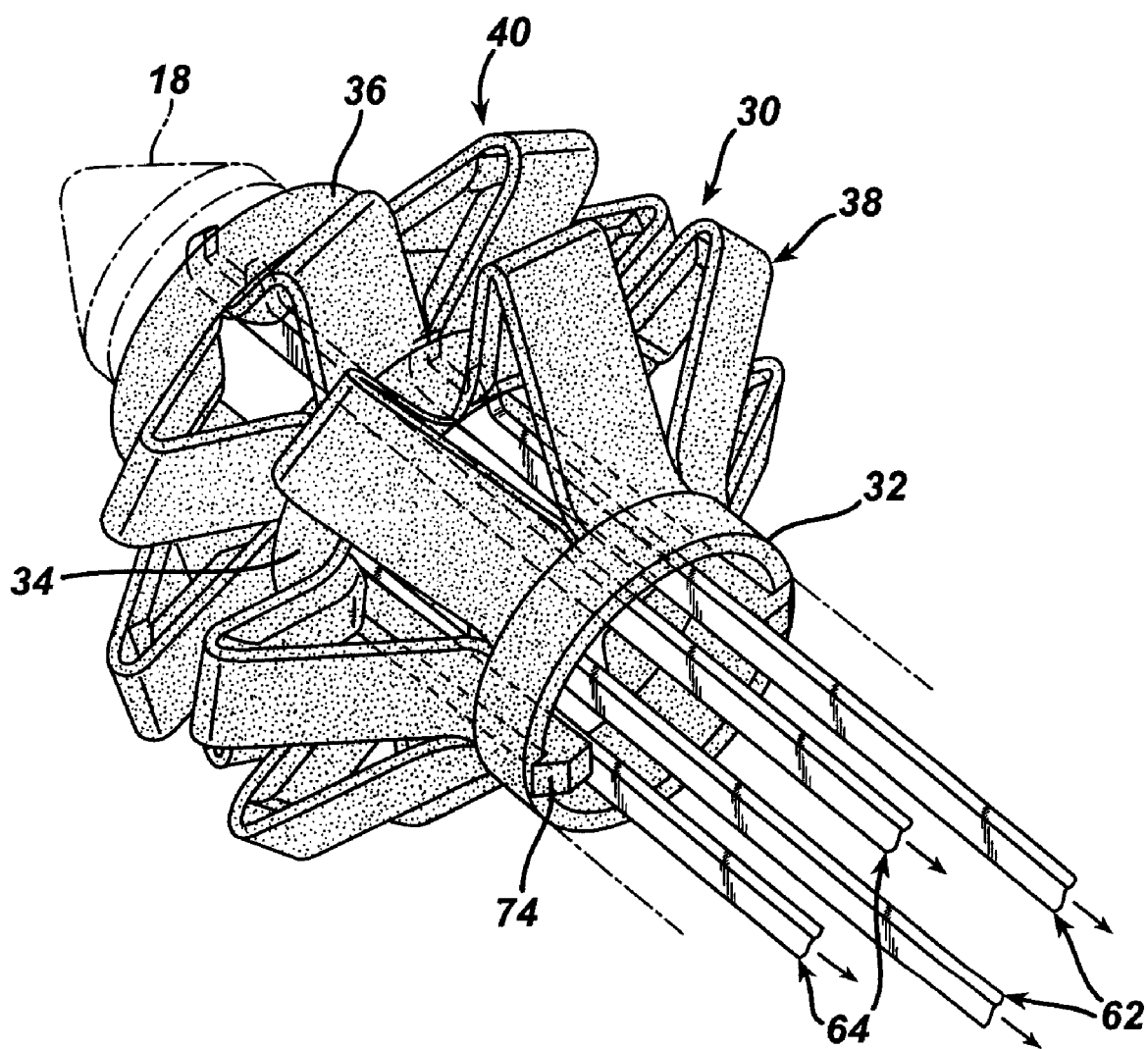
FIG. 6 is a perspective detail view of a fully actuated ring device and distal portion of the applier of FIG. 2.
Figure 7:
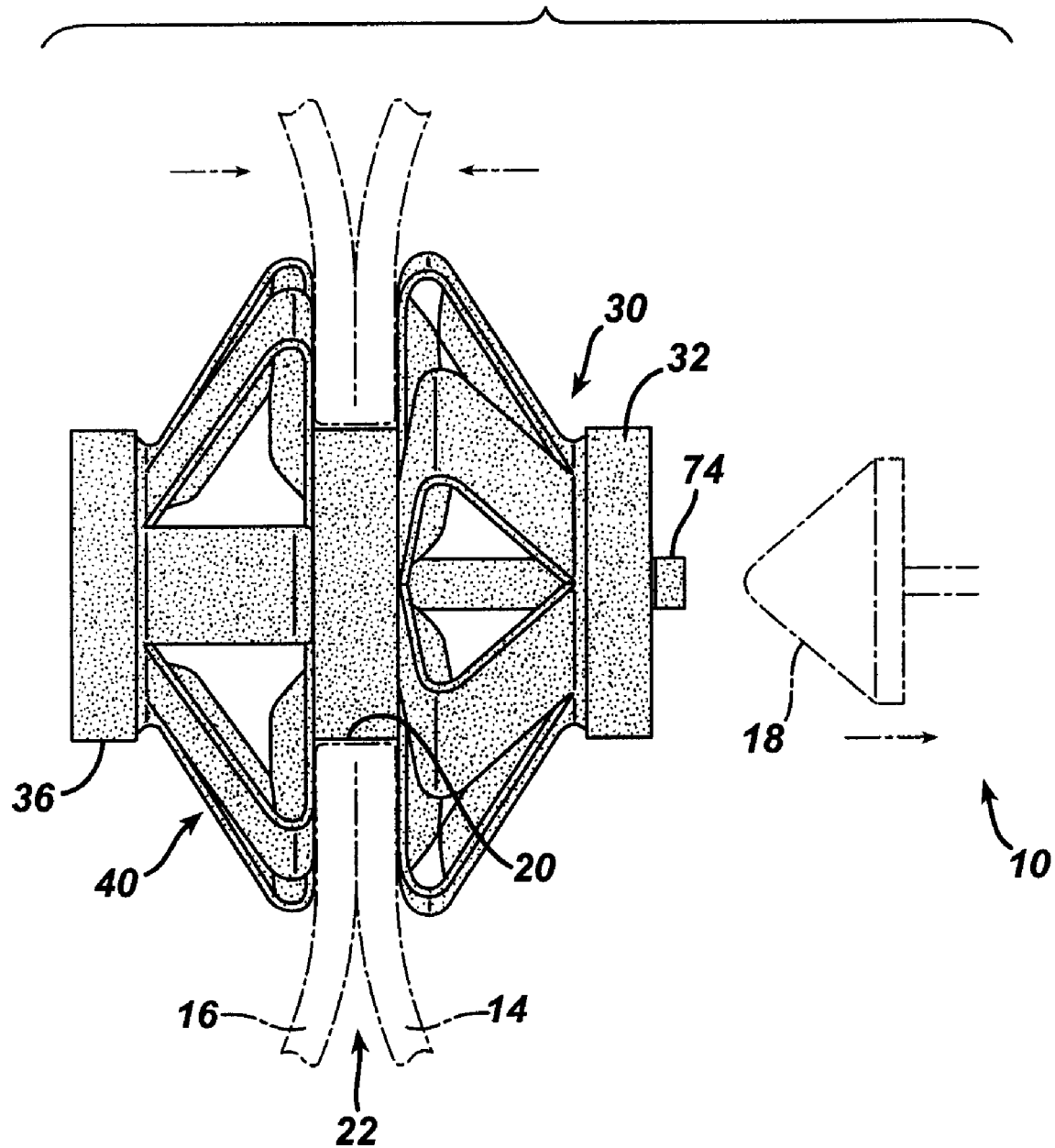
FIG. 7 is a side elevation view of the fully actuated and deployed ring device of FIG. 6.

In FIGS. 6-7, the ring device 30 has fully actuated. In FIG. 6, the actuating members 62, 64 have caused the locking hook 74 to lock the distal ring 36 to the proximal ring 32. It should be appreciated that this simple latching mechanism is illustrative and for clarity. A distally presented hook from the proximal ring 32 for instance may intermediately latch to the center ring 34 when the proximal arms 38 are partially actuated and latch to the distal ring 36 when the proximal arms 38 are fully actuated. In FIG. 7, the applier 10 has been withdrawn from the ring device 30. An advantage of having the locking hook exposed in the proximal lumen is convenient access for confirming latching and for reversing the closing of the device 30 in instances where a leak is detected after actuation (e.g., from the opening 20 out between the tissue walls 14, 16).

In use, a ring device 30 is received upon an actuating portion 24 of an implement portion 12 of an applier 10. Specifically, the proximal ring 32 of the device 30 rests against the shaft 56, a center ring actuating member 62 engages the center ring 34 of the device 30, and a distal ring actuating member 64 engages the distal ring 36 of the device 30. A clinician manipulates the handle 54 to insert the implement portion 12 through the cannula of a trocar, laparoscopic port, or through a lumen such as the esophagus to the anastomosis site 22. The tissue walls 14, 16 are proximately placed and the introducer tip 18 of the implement portion 12 passes through the opening 20 formed in these walls 14, 16. The introducer tip may include a piercing shape and/or electromagnetically or thermally enhanced cutting features to assist in forming the opening 20. Once the distal arms 40 of the device 30 are in the distal lumen, the distal ring slide control 60 may be proximally moved to actuate the distal arms into a partially actuated ring shape, latching the locking hook 74 to the center ring 34. The distal tissue wall 16 thus held may be drawn back proximally if necessary such that the proximal arms 38 reside within the first lumen. Drawing back the center ring slide control 58 thus partially actuates the proximal arms 38. If the positioning is correct, the slide controls 58, 60 may be fully slid, latching the locking hook 74 to the proximal ring and causing the proximal and distal arms 38, 40 to be fully actuated and disengaging the catches 70 that hold the applier 10 to the ring device 30. Then, the distal tip 18 of the applier is withdrawn from the ring device 30 leaving it deployed to form the anastomotic attachment. Over time, the tissue walls 14, 16 permanently heal together and the ring device 30 may be passed out of the digestive tract, especially if biofragmentable.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, aspects of the invention have application to surgical procedures performed endoscopically and laparoscopically, as well as an open procedure. Use herein of one of these or similar terms should not be construed to limit the present invention for use in only one category of surgical procedure.

For another example, although bariatric procedures for bypassing portions of a gastrointestinal tract are depicted, it should be appreciated that other surgical procedures may benefit by an anastomotic ring device having aspects described herein, such as for the bile duct and vascular bypasses.

As an additional example, instead of a center ring 34, the proximal arms 38 may attach to the distal arms 40 in an accordion-like fashion with the proximal ring 32 locking to the distal ring 36. Thus, the center portion of the device 30 at the tissue junction is capable of dilating, thereby further stabilizing the lumens to be anastomosed and preventing tissue slippage. This dilation may be effected either by the proximal and distal rings 32, 36 forcing a center portion to dilate with a wedging action or by making the inner arm segments 46-48 shorter than the outer arm segments 50-52.

As yet a further example, the rings 32, 34, 36 present an internally projecting contour that may be engaged by the catches 70 of the applier. Other engagements may be incorporated, such as a frangible adhesion between actuating members and one or more rings. In addition, a distal introducer tip may act as an anvil that may be withdrawn proximally to longitudinally compress the device, with features that may be radially withdrawn to thereafter allow the distal introducer tip to be removed from the ring device for deployment.

As yet another example, pads on the inner arm segments may be included to control the pressure profile on the tissue. Corners may be softened or smoothed to avoid any adverse effects of a traumatic contact to tissue.

What is claimed is:

1. A system comprising an applier with an anastomosis ring device having proximal, center, and distal rings connected respectively b proximal and distal hinged arms, the ring device having a generally cylindrical shape when unactuated and a rivet shape when actuated, the applier comprising:
   an elongate implement portion;
   a handle connected to the implement portion;
   a first actuating member of the elongate implement portion having a first set of prongs internally engaged to the distal ring of the anastomosis device, the first set of prongs being configured to deflectably disengage from the distal ring of the anastomosis ring device when the anastomosis ring device is actuated;
   an arresting member of the elongate implement portion engaged to the proximal ring of the anastomosis device;
   a second actuating member of the elongate implement portion having a second set of prongs internally engaged to the center ring of the anastomosis device, the second set of prongs being configured to deflectably disengage from the center ring of the anastomosis ring device when the anastomosis ring device is actuated; and
   first control coupled to the handle operably configured to cause proximal movement of the first actuating member and the distal ring engaged thereto toward the arresting member and toward the proximal ring;
   a second control coupled to the handle operably configured to cause proximal movement of the second actuating member and the center ring engaged thereto toward the arresting member and toward the proximal ring;
   wherein the first and second controls are operable to be selectively positioned to contemporaneously perform both of the following:
      (i) reduce a first longitudinal separation between the center ring and a selected one of the proximal and distal rings thereby causing actuating of the interposed hinged arms located between the center ring and the selected one of the proximal and distal rings of the ring device, and
      (ii) maintain a second longitudinal separation between the center ring and the other ring thereby preventing actuating of the interposed hinged arms located between the center ring and the other ring of the ring device to configure the anastomosis ring device into a partially actuated ring shape having one set of at least partially actuated arms and one set of unactuated arms; and
   wherein the first and second controls are further operable to be selectively positioned to reduce the longitudinal separation between the center ring and both the proximal ring and distal ring, causing actuating of all of the hinged arms of the anastomosis ring device.

2. The system of claim 1, wherein the first actuating member that is engaged to the distal ring of the ring device distally terminates in a catch.

3. The system of claim 2, wherein the prongs of the first actuating member that is engaged to the distal ring of the ring device includes a releasing surface responsive to an actuated condition of the ring device to disengage the first actuating member from the distal ring of the ring device.

4. The system of claim 1, further comprising a distal tip illuminator connected to the implement portion 5. The system of claim 1, wherein the implement portion is dimensionally sized for endoscopic surgical use.

6. An applier for an anastomotic ring device having a center circular portion longitudinally connected by a plurality of proximal arms to a proximal ring and by a plurality of distal arms to a distal ring, the ring expanding each plurality of arms by compressing a respective ring toward the center circular portion, the applier comprising:
   a first member having prongs operative to internally engage the distal ring;
   a second member having prongs operative to internally engage the center circular portion;
   a third member operative to engage the proximal ring; and
   a handle;
   a first control on the handle operatively configured to position at least one of the first, second and third members to separately actuate the plurality of distal arms; and
   a second control on the handle operatively configured to position at least one of the first, second and third members to separately actuate the plurality of proximal arms;

wherein when said center circular portion of said anastomotic ring device is engaged directly with said second member of said applier, movement of said center circular portion is constrained to movement of said second member;

wherein when said proximal ring and said distal ring are adjacent to said center circular portion, said first member and said second member are deflectably disengaged from said distal ring and said center circular portion.

7. The applier of claim 6, wherein the center circular portion of the ring device comprises a center ring, the second member engaged to the center ring.

8. The applier of claim 7, wherein the prongs of first and third members comprise a releasable engagement surface responsive to an actuated condition of the anastomotic device.

9. The applier of claim 6, further comprising a cannula distally supporting the first, second, and third members, wherein the cannula is proximally attached to the handle, operatively configured to distally receive the anastomotic device, and dimensioned for endoscopic use.

10. The system of claim 1, further comprising a locking member extending proximally from the distal ring, wherein the locking member is configured to selectively engage the center ring, thereby preventing distal movement of the distal ring relative to the center ring, when the distal ring has been moved toward the center ring to actuate the distal hinged arms.

11. The system of claim 10, wherein the locking member is further configured to selectively engage the proximal ring, thereby preventing distal movement of the distal ring relative to the proximal ring, when the center ring has been moved toward the proximal ring to actuate the proximal hinged arms.

* * * * *